United States Patent [19]

Cook

[11] Plant 4,890

[45] Sep. 28, 1982

[54] STRAWBERRY PLANT

[76] Inventor: Albert B. Cook, 320 N. Fifth St., Rockport, Ind. 47635

[21] Appl. No.: 218,732

[22] Filed: Dec. 22, 1980

[51] Int. Cl.[3] ..... A01H 5/03

[52] U.S. Cl. ..... Plt./48

[58] Field of Search ..... Plt./48

*Primary Examiner*—Robert E. Bagwill

*Attorney, Agent, or Firm*—Marmaduke A. Hobbs

[57] ABSTRACT

A strawberry plant which is vigorous and is a high producer of large fruit.

3 Drawing Figures

1

My invention relates to a new and distinct variety of strawberry plant. It is the result of a cross of [([(Canall×Twentieth Century)×Twentieth Century]-×Ogallala)×Oberschlesien]×Surecrop, made by me in 1969, at Grandview, Ind.

Since my discovery of the original plant, I have asexually reproduced a large number of plants from the original mother plant by rooted runners.

My object in the asexual propagation of the original mother plant was to determine the characteristics of the plant and of its fruit by the testing of a large number of plants. The distinguishing features of my new variety have proved to be permanent. My new variety has proved itself to have unusual possibilities because of its high productivity, its very vigorous growth, and its large fruit.

Figure 1:
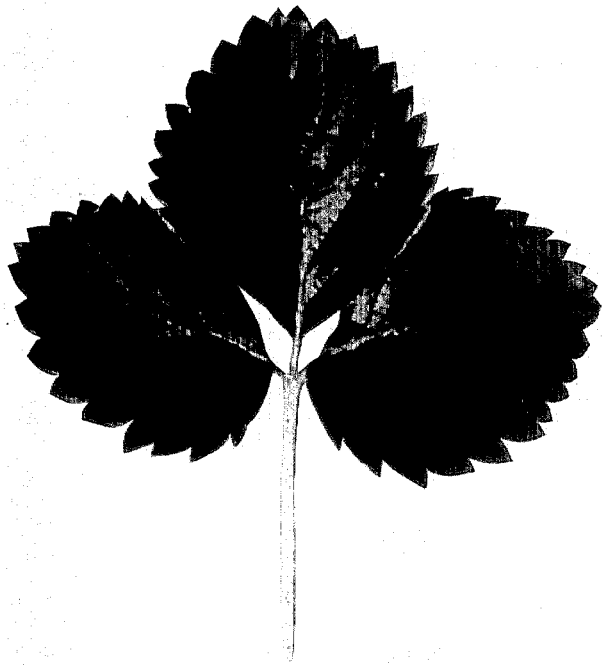
FIG. 1 shows a typical leaf in full color.
Figure 2:
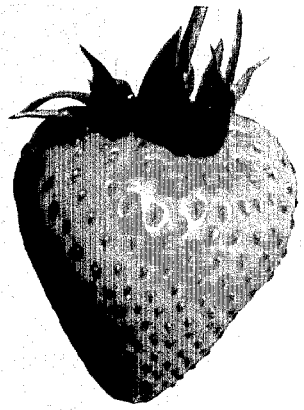
FIG. 2 is a berry of typical shape.
Figure 3:
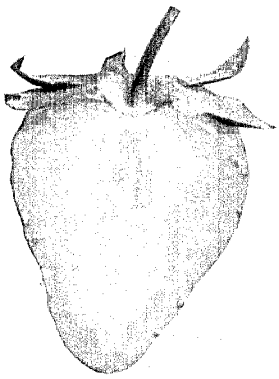
FIG. 3 illustrates a typical central longitudinal section of a berry.

In general, the distinct and new variety of strawberry plant, which is the subject of my invention and discovery, is characterized by its high productivity, its very vigorous growth, and its large fruit. These characteristics I now refer to in greater detail. Color plate references are according to Color Standards and Color Nomenclature by Robert Ridgeway.

Under the conditions at Grandview, Ind., and at Champaign, Ill., my new variety of plant is June-bearing and high in productivity, producing about 1 to 1¼ quarts of fruit per plant planted. In southwestern Michigan, it has produced up to 1½ quarts of fruit per plant planted. The plants are very vigorous and tall, measuring up to 12 inches in height and averaging about 10 to 11 inches. They produce many runners (about 30 to 40 per plant planted—slightly more than Guardian), making a wide row.

The leaves are medium green in color, or are approximately Forest Green (Plate XVII), or varying from Varley's Green (Plate XVIII) to Forest Green (Plate XVII) to Cerro Green (Plate V), depending mainly on soil fertility, but also depending on other soil conditions, exposure, and weather and climatic conditions. The leaves are many and very large (up to 8 inches in width and averaging about 6 to 7 inches), occasionally making very dense foliage. They are glossy, slightly cupped, and medium in rugosity. The terminal leaflet overlaps the lateral leaflets. Most lateral leaflets do not overlap at

2 the base of the leaf; however, the lateral leaflets have relatively short petiolules. The flowers are perfect. The date of the first blossoms in 1980 in southwestern Michigan was May 18.

At Grandview, Ind., and at Champaign, Ill., my new variety of strawberry plant begins to mature its fruit in midseason, about the same time as Guardian and 4 to 5 days later than Surecrop. Under conditions of very dense foliage, the first picking is a few days later. The date of the first picking in 1980 in southwestern Michigan was June 15. The harvesting period is medium in length or about 14 to 21 days. The berries are well formed throughout the bearing season.

The fruit is medium red (darker than Guardian and Surecrop), or is approximately Nepal Red (Plate I), or varying from Jasper Red (Plate XIII) to Nepal Red (Plate I) to Carmine Red (Plate I), depending mainly on exposure, but also depending on soil, weather, and climatic conditions. The fruit is large (up to 1¾ inches in diameter and averaging about 1¼ to 1½ inches), and the size is maintained well during the picking season. The berries are conic in shape, with a few late berries being long conic. In general, the fruit is not necked; however, occasionally a large berry is slightly necked with an enlargement of the flesh at the base of up to 20% of the stamens. The fruit is glossy and firm.

The calyx is large. The achenes are about flush with the surface to slightly raised, and are yellow to red depending on exposure.

Under the conditions existing where I have reproduced and tested my new variety of strawberry plant, the flesh of the berry is medium light red to medium red (including the core), with a thin whitish area around the core. The flesh of Guardian and Surecrop is lighter red. Some berries have a very slight hollow area in the core. The fruit is relatively sweet, and is slightly above average in flavor.

My new variety of strawberry plant is not especially resistant to any of the diseases. The strawberry above described, and the plant producing it, of course, may vary in slight details, depending on soil, weather, and climatic conditions.

What I claim is:

1. A new and distinct variety of strawberry plant substantially as herein shown and described, characterized by its high productivity, its very vigorous growth, and its large fruit.

* * * * *